United States Patent [19]
Yuan et al.

[11] Patent Number: 5,847,136
[45] Date of Patent: *Dec. 8, 1998

[54] DEAZAPURINE DERIVATIVES; A NEW CLASS OF CRF1 SPECIFIC LIGANDS

[75] Inventors: Jun Yuan, Clinton; Alan Hutchison, Madison, both of Conn.

[73] Assignee: Neurogen Corporation, Branford, Conn.

[*] Notice: The term of this patent shall not extend beyond the expiration date of Pat. No. 5,644,057.

[21] Appl. No.: 881,960

[22] Filed: Jun. 25, 1997

Related U.S. Application Data

[63] Continuation of Ser. No. 439,874, May 12, 1995, Pat. No. 5,644,057.

[51] Int. Cl.⁶ .................................................. C07D 487/02
[52] U.S. Cl. ........................................ 544/280; 546/276.7
[58] Field of Search .......................... 544/280; 546/276.7

[56] References Cited

U.S. PATENT DOCUMENTS 4,605,642  8/1986  Rivier et al. ............................. 514/12
5,063,245  11/1991  Abreu et al. ............................ 514/404

*Primary Examiner*—Joseph K. McKane
*Attorney, Agent, or Firm*—McDonnell Boehnen Hulbert & Berghoff

[57] ABSTRACT

Disclosed are compounds of the formula

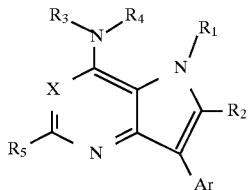

wherein

Ar represents an aryl or heteroaryl group; and $R_1$, $R_2$, $R_3$, $R_4$, and $R_5$ represent organic or inorganic substituents, which compounds are highly selective partial agonists or antagonists at human CRF1 receptors and, thus, are useful in the diagnosis and treatment of treating stress related disorders such as post trumatic stress disorder (PTSD) as well as depression, headache and anxiety.

8 Claims, No Drawings

DEAZAPURINE DERIVATIVES; A NEW CLASS OF CRF1 SPECIFIC LIGANDS

This is a continutation of application Ser. No. 08/439,874 filed May 12, 1995, now U.S. Pat. No. 5,644,057.

BACKGROUND OF THE INVENTION

1. Field of the Invention

This invention relates to novel substituted deazapurine derivatives which selectively bind to CRF receptors. More specifically, it relates to pyrrolo[3,2-d]pyrimidin-4-amines, pyrrolo[3,2-b]pyridin-4-amines, and pyrrolo[3,2-b]pyridin-4-amines, and their use as antagonists of Corticotropin-Releasing Factor in the treatment of various disease states.

2. Description of the Related Art

Corticotropin-releasing factor (CRF) antagonists are mentioned in U.S. Pat. Nos. 4,605,642 and 5,063,245 referring to peptides and pyrazoline derivatives, respectively. The importance of CRF antagonists is described in the literature, for example, as discussed in U.S. Pat. No. 5,063,245, which is incorporated herein by reference in its entirety. CRF antagonists are considered effective in the treatment of a wide range of diseases including stress-related illnesses, such as stress-induced depression, anxiety, and headache. Other diseases considered treatable with CRF antagonists are discussed in U.S. Pat. No. 5,063,245 and Pharm. Rev., 43: 425–473 (1991).

International application WO 9413676 A1 discloses pyrrolo[2,3-d]pyrirnidines as having Corticotropin-Releasing Factor antagonist acitivity. J. Het. Chem. 9, 1077 (1972) describes the synthesis of 9-Phenyl-pyrrolo[3,2-d] pyrimidines.

SUMMARY OF THE INVENTION

This invention provides novel compounds of Formula I which interact with CRF receptors.

The invention provides pharmaceutical compositions comprising compounds of Formula I. It further relates to the use of such compounds in treating stress related disorders such as post trumatic stress disorder (PTSD) as well as depression, headache and anxiety. Accordingly, a broad embodiment of the invention is directed to a compound of Formula I:

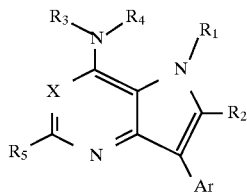

wherein
- Ar is phenyl, where the phenyl group is mono-, di-, or trisubstituted with halogen, hydroxy, lower alkyl, or lower alkoxy, with the proviso that at least one of the ortho positions of the phenyl group is substituted; or
- Ar is 2-, 3-, or 4-pyridyl, 2- or 3- thienyl, 4- or 5-pyrimidyl, each of which is optionally mono-, di-, or trisubstituted with halogen, hydroxy, lower alkyl, or lower alkoxy, with the proviso that at least one of the ortho positions of the Ar substituent is substituted;
- X is CH or nitrogen;
- $R_1$ is lower alkyl;
- $R_2$ is hydrogen, halogen, lower alkyl, lower alkoxy, or thioalkoxy; or
- $R_1$ and $R_2$ taken together represent $—(CH_2)_n—A—(CH_2)_m—$,
  where n is 2, 3 or 4, A is methylene, oxygen, sulfur or $NR_6$, where $R_6$ is lower alkyl, and
  m is 0, 1 or 2;
- $R_3$ and $R_4$ are the same or different and represent hydrogen or lower alkyl; phenyl, 2-, 3-, or 4-pyridyl, 2-, or 3-thienyl, or 2-, 4-, or 5-pyrimidyl, each of which is optionally mono- or disubstituted with halogen, hydroxy, lower alkyld, or lower alkoxy; phenyl lower alkyl, 2-, 3-, or 4-pyridyl lower alkyl, 2- or 3-thienyl lower alkyl, or 2-, 4-, or 5-pyrimidyl lower alkyl; cycloalkyl having 3–8 carbon atoms or cycloalkyl lower alkyl where the cycloalkyl portion has 3–8 carbon atoms; 2-hydroxyethyl or 3-hydroxypropyl optionally mono or disubstituted with lower alkyl with the proviso that not both $R_3$ and $R_4$ are hydrogen; or
- $R_3$ and $R_4$ taken together represent $—(CH_2)_n—A—(CH_2)_m—$
  where n is 2, or 3,
  A is methylene, 1,2 phenylene, oxygen, sulfur or $NR_6$, wherein $R_6$ is lower alkyl, phenyl, 2-, 3-, or 4-pyridyl, 2-or 3-thienyl or 2-, 4-, or 5-pyrimidyl, phenyl lower alkyl, 2-, 3-, or 4-pyridyl lower alkyl, 2-or 3-thienyl lower alkyl, or 2-, 4-, or 5-pyrimidyl lower alkyl; and
  m is 1, 2 or 3; and
- $R_5$ is hydrogen, halogen, lower alkyl, lower alkoxy, or thioalkoxy.

These compounds, i.e., substituted deazapurine derivatives, are highly selective partial agonists or antagonists at CRF receptors and are useful in the diagnosis and treatment of stress related disorders such as post trumatic stress disorder (PTSD) as well as depression and anxiety.

Thus, the invention provides compounds, including pharmaceutically acceptable salts of the compounds of formula I, and pharmaceutical compositions for use in treating disease states associated with Corticotropin-releasing factor. The invention further provides methods including animal models relevant to the evaluation of the interaction of the compounds of the invention with CRF receptors. This interaction results in the pharmacological activities of these compounds.

DETAILED DESCRIPTION OF THE INVENTION

In this document, all temperatures will be stated in degrees Celsius. All amounts, ratios, concentrations, proportions and the like will be stated in weight units, unless otherwise stated, except for ratios of solvents, which are in volume units.

In addition to compounds of general formula I described above, the invention encompasses compounds of general formula IA:

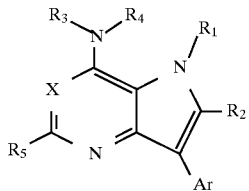

wherein
- Ar is phenyl, 2-, 3-, or 4-pyridyl, 2- or 3-thienyl, 4- or 5-pyrimidyl, each of which is mono-, di-, or trisubstituted with halogen, hydroxy, lower alkyl, or lower alkoxy, with the proviso that at least one of the ortho positions of the Ar substituent is substituted;

X is CH or nitrogen;

$R_1$ is lower alkyl;

$R_2$ is hydrogen, halogen, lower alkyl, lower alkoxy, or thioalkoxy; or $R_1$ and $R_2$ taken together represent —$(CH_2)_n$—A—$(CH_2)_m$—,
where n is 2, 3 or 4, A is methylene, oxygen, sulfur or $NR_6$, where $R_6$ is lower alkyl, and
m is 0, 1 or 2;

$R_3$ and $R_4$ are the same or different and represent
hydrogen or lower alkyl;
phenyl, 2-, 3-, or 4-pyridyl, 2-, or 3-thienyl, or 2-, 4-, or 5-pyrimidyl, each of which is mono- or disubstituted with halogen, hydroxy, lower alkyl, or lower alkoxy;
phenyl lower alkyl, 2-, 3-, or 4-pyridyl lower alkyl, 2- or 3-thienyl lower alkyl, or 2-, 4-, or 5-pyrimidyl lower alkyl;
cycloalkyl having 3–8 carbon atoms or cycloalkyl lower alkyl where the cycloalkyl portion has 3–8 carbon atoms;
2-hydroxyethyl or 3-hydroxypropyl optionally mono or disubstituted with lower alkyl with the proviso that not both $R_3$ and $R_4$ are hydrogen; or $R_3$ and $R_4$ taken together represent —$(CH_2)_n$—A—$(CH_2)_m$—
where n is 2, or 3,
A is methylene, 1,2 phenylene, oxygen, sulfur or $NR_6$, wherein $R_6$ is lower alkyl, phenyl, 2-, 3-, or 4-pyridyl, 2- or 3-thienyl or 2-, 4-, or 5-pyrimidyl, phenyl lower alkyl, 2-, 3-, or 4-pyridyl lower alkyl, 2- or 3-thienyl lower alkyl, or 2-, 4-, or 5-pyrimidyl lower alkyl, and
m is 1, 2 or 3; and $R_5$ is hydrogen, halogen, lower alkyl, lower alkoxy, or thioalkoxy.

In the compounds of the invention, preferred $NR_3R_4$ groups include the following:

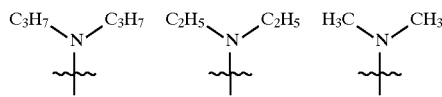

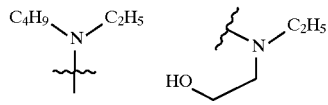

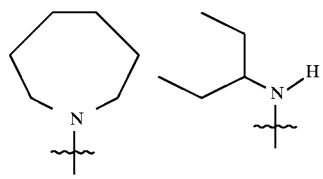

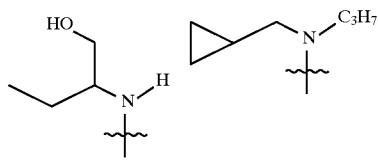

Preferred compounds of formula I are those where $R_1$ is methyl, ethyl or propyl or isopropyl; $R_2$ is lower alkyl, halogen, or thio lower alkyl; $R_5$ is lower alkyl or halogen; and $R_7$, $R_8$, and $R_9$ represent methyl, ethyl, propyl or isopropyl.

The invention provides compounds of formula II

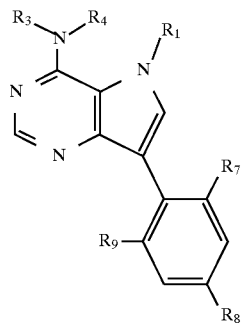

wherein $R_4$ represents hydrogen or lower alkyl;

$R_1$, $R_7$, $R_8$, and $R_9$ represent lower alkyl; and $R_3$ represents lower alkyl, or cycloalkyl lower alkyl.

Preferred compounds of formula II are those where $R_1$ is methyl, ethyl or propyl or isopropyl; and $R_7$, $R_8$, and $R_9$ represent methyl, ethyl, propyl or isopropyl. Particularly preferred compounds of formula II are those where $R_1$ is methyl, and $R_7$, $R_8$, and $R_9$ represent methyl.

The invention provides compounds of formula III

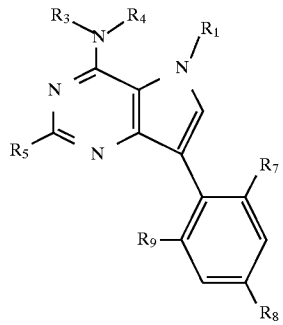

wherein $R_4$ represents hydrogen or lower alkyl;

$R_1$, $R_7$, $R_8$, and $R_9$ represent lower alkyl; and $R_3$ represents lower alkyl, or cycloalkyl lower alkyl; and $R_5$ is lower alkyl, halogen, or thio lower alkyl.

Preferred compounds of formula III are those where $R_1$ is methyl, ethyl or propyl or isopropyl; $R_5$ is halogen or thio lower alkyl; and $R_7$, $R_8$, and $R_9$ represent methyl, ethyl, propyl or isopropyl. Particularly preferred compounds of formula III are those where $R_1$ is methyl; $R_5$ is halogen, thiomethyl; and $R_7$, $R_8$, and $R_9$ represent methyl, ethyl, propyl or isopropyl.

The invention provides compounds of formula IV

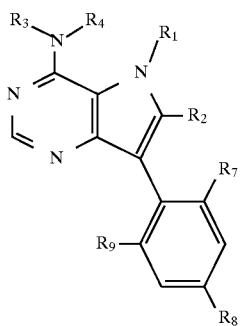

IV wherein

R$_4$ represents hydrogen or lower alkyl;

R$_1$, R$_7$, R$_8$, and R$_9$ represent lower alkyl; and

R$_3$ represents lower alkyl, or cycloalkyl lower alkyl; and

R$_5$ is lower alkyl, halogen, or thio lower alkyl.

Preferred compounds of formula IV are those where R$_1$ is methyl, ethyl or propyl or isopropyl; R$_5$ is halogen or thio lower alkyl; and R$_7$, R$_8$, and R$_9$ represent methyl, ethyl, propyl or isopropyl. Particularly preferred compounds of formula IV are those where R$_1$ is methyl; R$_5$ is halogen, thiomethyl; and R$_7$, R$_8$, and R$_9$ represent methyl, ethyl, propyl or isopropyl.

The invention provides compounds of formula V

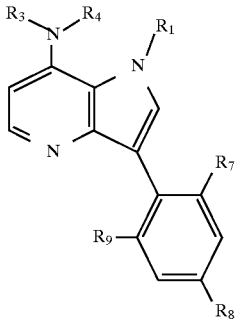

wherein

R$_4$ represents hydrogen or lower alkyl;

R$_1$, R$_7$, R$_8$, and R$_9$ represent lower alkyl; and

R$_3$ represents lower alkyl, or cycloalkyl lower alkyl.

Preferred compounds of formula V are those where R$_1$ is methyl, ethyl or propyl or isopropyl; and R$_7$, R$_8$, and R$_9$ represent methyl, ethyl, propyl or isopropyl. Particularly preferred compounds of formula V are those where R$_1$ is methyl, and R$_7$, R$_8$, and R$_9$ represent methyl.

The invention provides compounds of formula VI

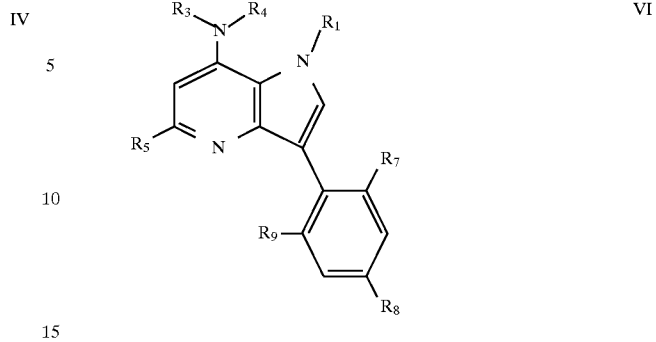

VI wherein

R$_4$ represents hydrogen or lower alkyl;

R$_1$, R$_7$, R$_8$, and R$_9$ represent lower alkyl; and

R$_3$ represents lower alkyl, or cycloalkyl lower alkyl; and

R$_5$ is lower alkyl, halogen, or thio lower alkyl.

Preferred compounds of formula VI are those where R$_1$ is methyl, ethyl or propyl or isopropyl; R$_5$ is halogen or thio lower alkyl; and R$_7$, R$_8$, and R$_9$ represent methyl, ethyl, propyl or isopropyl. Particularly preferred compounds of formula VI are those where R$_1$ is methyl; R$_5$ is halogen, thiomethyl; and R$_7$, R$_8$, and R$_9$ represent methyl, ethyl, propyl or isopropyl.

The invention provides compounds of formula VII:

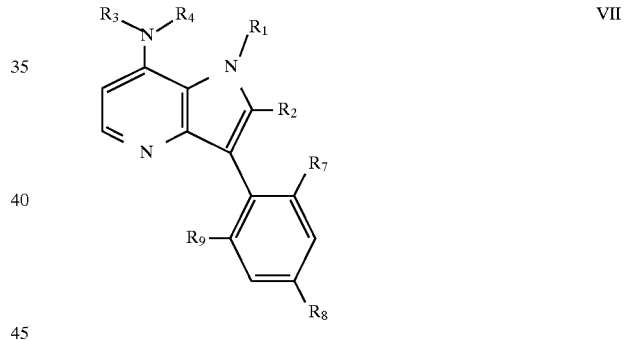

VII wherein

R$_4$ represents hydrogen or lower alkyl;

R$_1$, R$_7$, R$_8$, and R$_9$ represent lower alkyl; and

R$_3$ represents lower alkyl, or cycloalkyl lower alkyl; and

R$_5$ is lower alkyl, halogen, or thio lower alkyl.

Preferred compounds of formula VII are those where R$_1$ is methyl, ethyl or propyl or isopropyl; R$_5$ is halogen or thio lower alkyl; and R$_7$, R$_8$, and R$_9$ represent methyl, ethyl, propyl or isopropyl. Particularly preferred compounds of formula VII are those where R$_1$ is methyl; R$_5$ is halogen, thiomethyl; and R$_7$, R$_8$, and R$_9$ represent methyl, ethyl, propyl or isopropyl.

In each of formulas II to VII, NR$_3$R$_4$ optionally represents —(CH$_2$)$_n$—A—(CH$_2$)$_m$— where m, n, and A are as defined above for formula I.

The invention also provides compounds of formula VIII:

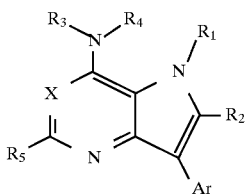

wherein
Ar is phenyl, 2-, 3-, or 4-pyridyl, 2- or 3-thienyl, 4- or 5-pyrimidyl, each of which is mono-, di-, or trisubstituted with halogen, hydroxy, lower alkyl, or lower alkoxy, with the proviso that at least one of the ortho positions of the Ar substituent is substituted;
X is CH or nitrogen;
$R_1$ is lower alkyl;
$R_2$ is hydrogen, halogen, lower alkyl, lower alkoxy, or thioalkoxy; or
$R_3$ and $R_4$ are the same or different and represent hydrogen or lower alkyl; phenyl, 2-, 3-, or 4-pyridyl, 2-, or 3-thienyl, or 2-, 4-, or 5-pyrimidyl, each of which is mono- or disubstituted with halogen, hydroxy, lower alkyl, or lower alkoxy; phenyl lower alkyl, 2-, 3-, or 4-pyridyl lower alkyl, 2- or 3-thienyl lower alkyl, or 2-, 4-, or 5-pyrimidyl lower alkyl; cycloalkyl having 3–8 carbon atoms or cycloalkyl lower alkyl where the cycloalkyl portion has 3–8 carbon atoms; 2-hydroxyethyl or 3-hydroxypropyl optionally mono or disubstituted with lower alkyl with the proviso that not both $R_3$ and $R_4$ are hydrogen;
$R_3$ and $R_4$ taken together represent —$(CH_2)_n$—A—$(CH_2)_m$—
where n is 2, or 3,
A is methylene, 1,2 phenylene, oxygen, sulfur or $NR_6$, wherein $R_6$ is lower alkyl; and
m is 1, 2 or 3; and
$R_5$ is hydrogen, halogen, lower alkyl, lower alkoxy, or thioalkoxy.

In addition, the invention provides compounds of formula IX:

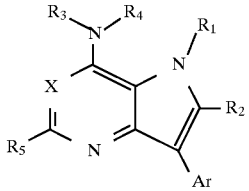

wherein
Ar is phenyl mono-, di-, or trisubstituted with halogen, hydroxy, lower alkyl, or lower alkoxy, with the proviso that at least one of the ortho positions of the Ar substituent is substituted;
X is nitrogen;
$R_1$ is lower alkyl;
$R_2$ is hydrogen, halogen, lower alkyl, lower alkoxy, or thioalkoxy; or
$R_3$ and $R_4$ are the same or different and represent hydrogen or lower alkyl;
cycloalkyl having 3–8 carbon atoms or cycloalkyl lower alkyl where the cycloalkyl portion has 3–8 carbon atoms;
2-hydroxyethyl or 3-hydroxypropyl optionally mono or disubstituted with lower alkyl with the proviso that not both $R_3$ and $R_4$ are hydrogen; or $R_3$ and $R_4$ taken together represent —$(CH_2)_n$—A—$(CH_2)_m$—
where n is 2, or 3,
A is methylene, 1,2 phenylene, oxygen, sulfur or $NR_6$, wherein $R_6$ is lower alkyl; and
m is 1, 2 or 3;
$R_5$ is hydrogen, halogen, lower alkyl, lower alkoxy, or thioalkoxy.

Further, the invention provides compounds of formula X:

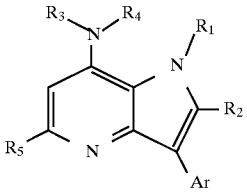

wherein
Ar is phenyl mono-, di-, or trisubstituted with halogen, hydroxy, lower alkyl, or lower alkoxy, with the proviso that at least one of the ortho positions of the Ar substituent is substituted;
$R_1$ is lower alkyl;
$R_2$ is hydrogen, halogen, lower alkyl, lower alkoxy, or thioalkoxy; or
$R_3$ and $R_4$ are the same or different and represent hydrogen or lower alkyl;
cycloalkyl having 3–8 carbon atoms or cycloalkyl lower alkyl where the cycloalkyl portion has 3–8 carbon atoms;
2-hydroxyethyl or 3-hydroxypropyl optionally mono or disubstituted with lower alkyl with the proviso that not both $R_3$ and $R_4$ are hydrogen; or
$R_3$ and $R_4$ taken together represent —$(CH_2)_n$—A—$(CH_2)_m$—
where n is 2, or 3,
A is methylene, 1,2 phenylene, oxygen, sulfur or $NR_6$, wherein $R_6$ is lower alkyl; and
m is 1, 2 or 3;
$R_5$ is hydrogen, halogen, lower alkyl, lower alkoxy, or thioalkoxy.

Representative compounds of the present invention, which are encompassed by Formula I, include, but are not limited to the compounds in FIG. I and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By aryl or "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy.

By aryl or "Ar" is also meant heteroaryl groups where heteroaryl is defined as 5, 6, or 7 membered aromatic ring systems having at least one hetero atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be substituted with, e.g., halogen, lower alkyl, lower alkoxy, lower alkylthio, trifluoromethyl, lower acyloxy, aryl, heteroaryl, and hydroxy.

By alkyl and lower alkyl is meant straight and branched chain alkyl groups having from 1–6 carbon atoms. Specific examples of alkyl groups are methyl, ethyl, propyl, isopropyl, n-butyl, isobutyl, tert-butyl, sec-butyl, neopentyl and n-pentyl.

By lower alkoxy and alkoxy is meant straight and branched chain alkoxy groups having from 1–6 carbon atoms.

By thioalkoxy is meant a straight or branched chain alkoxy group having from 1–6 carbon atoms and a terminal sulfhydryl, i.e., —SH, moiety.

By thio lower alkyl as used herein is meant a lower alkyl group having a terminal sulfhydryl, i.e., —SH, group.

By halogen is meant fluorine, chlorine, bromine and iodine.

Representative examples of pyrrolo[3,2-d]pyrimidines according to the invention are shown in Table 1 below.

TABLE 1[1]

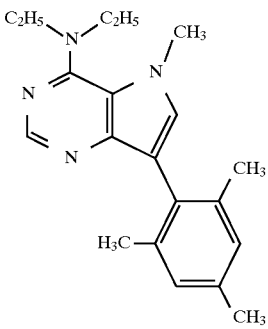

1

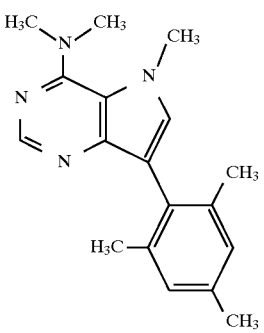

2

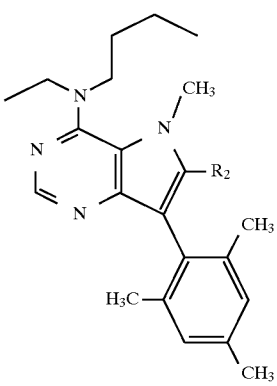

3

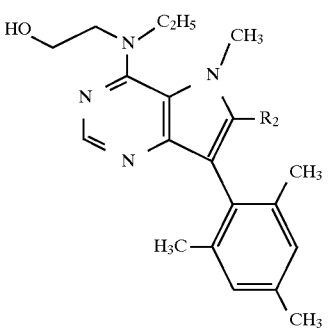

4

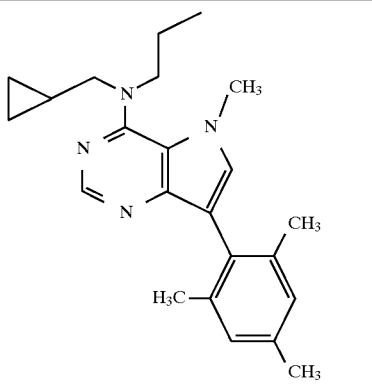

5

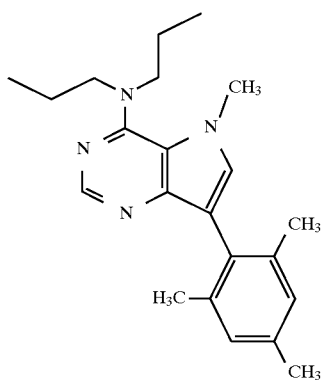

6

TABLE 1¹-continued
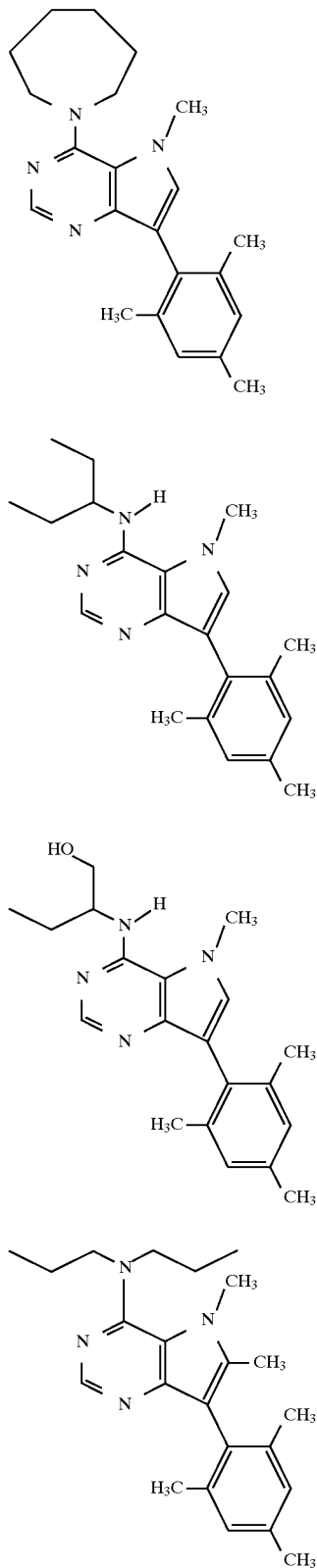
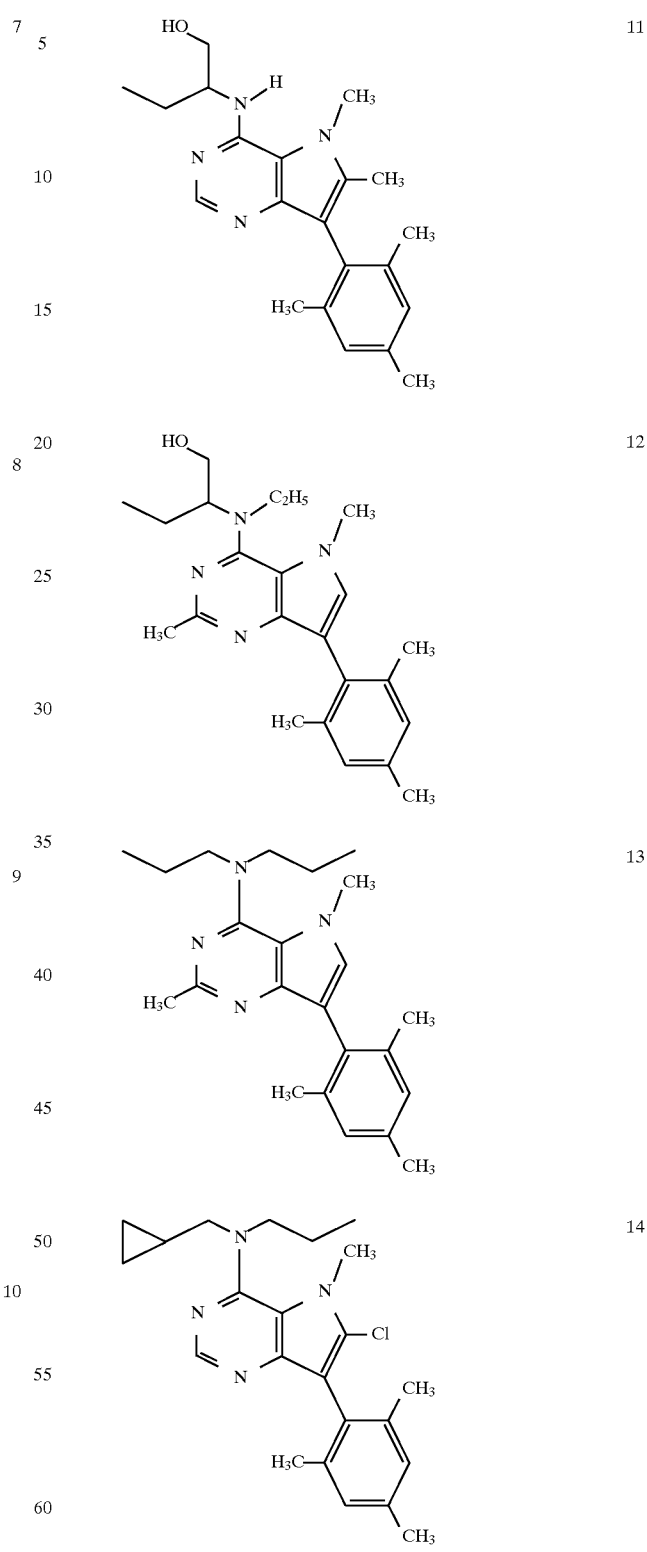

TABLE 1[1]-continued

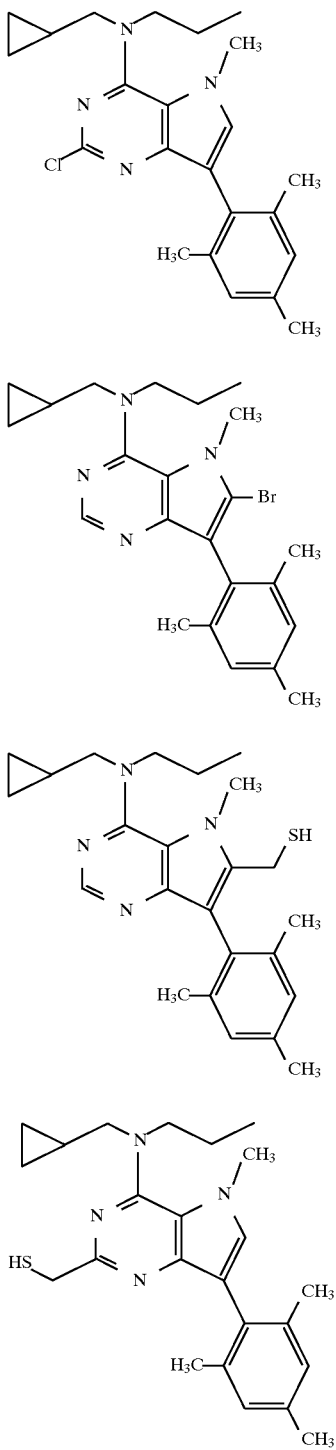

TABLE 1[1]-continued

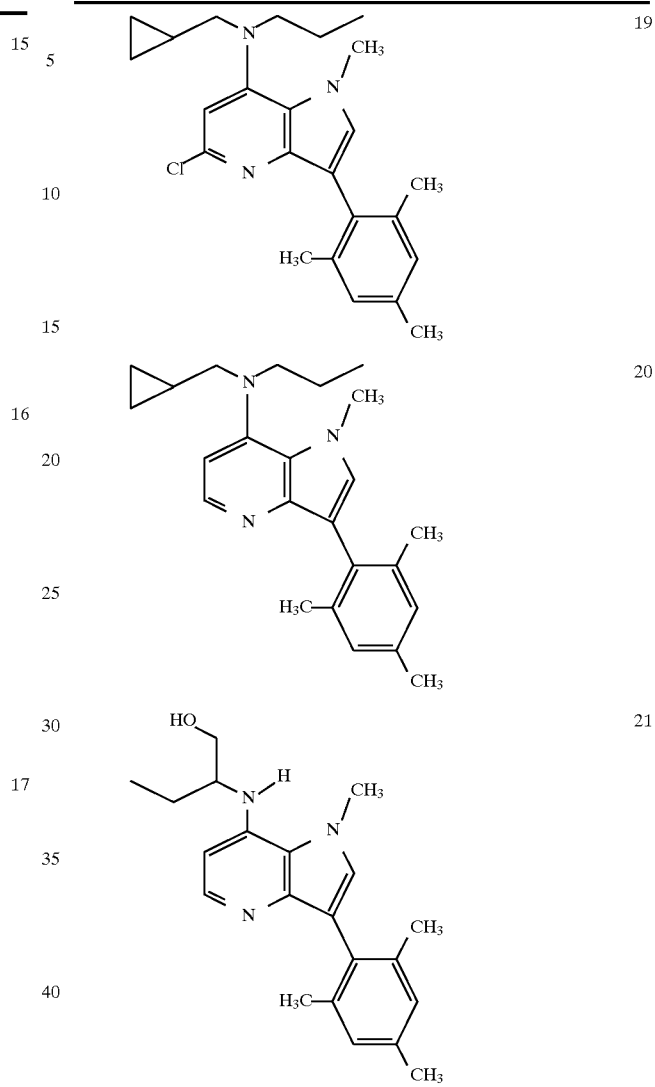

[1] The number below each compound is its compound number.

The pharmaceutical utility of compounds of this invention is indicated by the following assay for CRF receptor activity.

Assay for CRF Receptor Binding Activity

CRF receptor binding was performed using a modified version of the assay described by Grigoriadis and De Souza (Biochemical, Pharmnacological, and Autoradiographic Methods to Study Corticotropin-Releasing Factor Receptors. *Methods in Netirosciences*, Vol. 5, 1991). Membrane pellets containing CRF receptors were resuspended in 50 mM Tris buffer pH 7.7 containing 10 mM $MgCl_2$ and 2mM EGTA and centrifuged for 10 minutes at 48000 g. Membranes were washed again and brought to a final concentration of 1500 μg/ml in binding buffer (Tris buffer above with 0.1% BSA, 0.15 mM bacitracin and 0.01 mg/ml aprotinin.). For the binding assay, 100 μl of the membrane preparation was added to 96 well microtube plates containing 100 μl of $^{125}$I-CRF (SA 2200 Ci/mmol, final concentration of 100 pM) and 50 μl of drug. Binding was carried out at room temperature for 2 hours. Plates were then harvested on a Brandel 96 well cell harvester and filters were counted for gamma emissions on a Wallac 1205 Betaplate liquid scintillation counter. Non specific binding was defined by 1 μM cold CRF. $IC_{50}$ values were calculated with the non-linear curve fitting program RS/1 (BBN Software Products Corp., Cambridge, Mass.). The binding characteristics for examples from this patent are shown in Table 2.

TABLE 2

| Compound Number[2] | $IC_{50}$ (uM) |
| --- | --- |
| 1 | 0.110 |
| 5 | 0.500 |

[2]Compound numbers relate to compounds shown above in Table 1.

Compounds 1 and 5 are particularly preferred embodiments of the present invention because of their potency in binding to CRF receptors.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the torn of oil-in-water emulsions. The oily phase may be a vegetable oil, for example olive oil or arachis oil, or a mineral oil, for example liquid paraffin or mixtures of these. Suitable emulsifying agents may be naturally-occuring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile. fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative illustration of methods suitable for the preparation of compounds of the present invention is shown in Schemes I and II. Those having skill in the art will recognize that the starting materials may be varied and additional steps employed to produce compounds encompassed by the present invention.

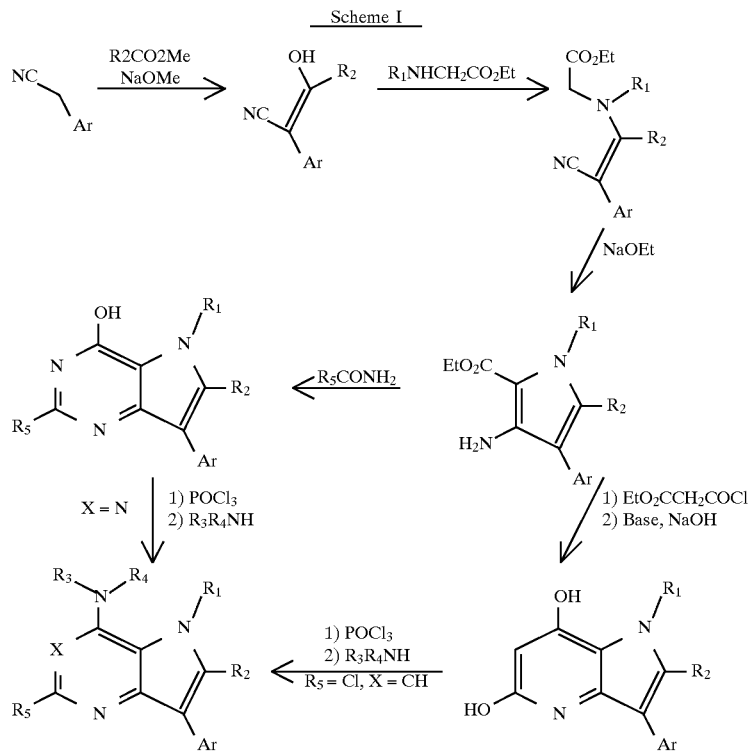

wherein Ar, $R_1$, $R_2$, $R_3$, $R_4$, and $R_5$ are as defined above for formula I.

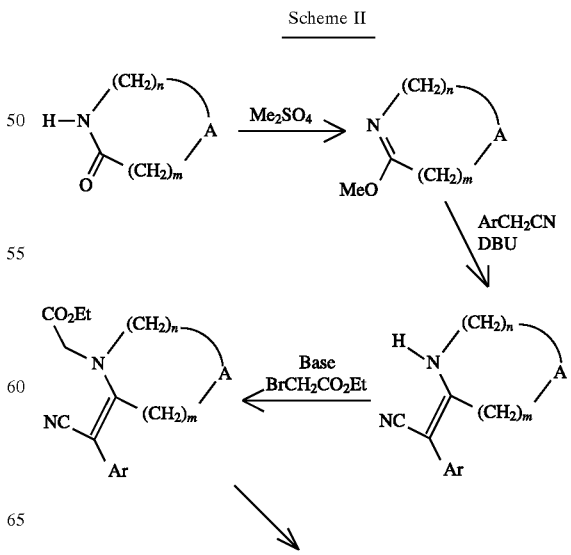

-continued
Scheme II

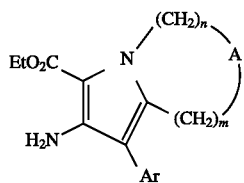

where Ar, n, m, and A are as defined above for formula I.

The disclosures in this application of all articles and references, including patents, are incorporated herein by reference.

The invention is illustrated further by the following examples which are not to be construed as limiting the invention in scope or spirit to the specific procedures and compounds described in them.

EXAMPLE IA

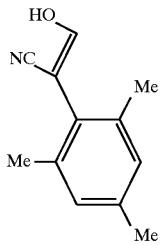

To a stirred mixture of sodium methoxide (2.78 g, 51 mmol) and ethyl formate (4.0 g, 54 mmol) in 100 mL of benzene was added 2,4,6 trimethylphenylacetonitrile (8.0 g, 50 mmol) over 5 min. After stirring for an additional hour it was treated with water (100 mL) and the layers were separated. The aqueous layer was separated and acidified with 10% HCl and extracted with ethyl acetate. After drying the solvent was removed in vacuo to afford a-formyl-2,4,6-trimethylphenylacetonitrile as colorless crystals melting at 120°–122° C.

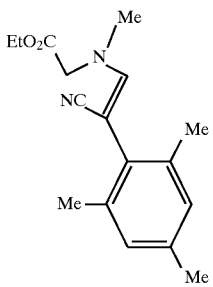

EXAMPLE IB

A mixture of a-formyl-2,4,6 trimethylphenylacetonitrile (4.5 g, 24 mmol) and sarcosine ethyl ester hydrochloride (3.7 g, 24 mmol) in 100 mL of benzene was refluxed in a Dean-Stark apparatus for 16 h. The solvent was removed in vacuo to afford N-Methyl-N-[2-(2,4,6-trimethylphenyl)-2-cyanovinyl]-glycine ethyl ester as a pale yellow oil.

EXAMPLE IC

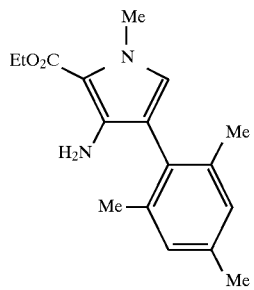

A solution of N-Methyl-N-[2-(2,4,6-trimethylphenyl)-2-cyanovinyl]-glycine ethyl ester (6.8 g, 24 mmol) in 0.28M ethanolic sodium ethoxide (100 mL) was heated at 70° C. for 6 h. The reaction was cooled and evaporated in vacuo. The residue was treated with water and neutralized with acetic acid and the product was extracted with ethyl acetate. After drying the solvent was removed in vacuo to afford 3-Amino-2-ethoxycarbonyl-2-methyl-4-(2,4,6-trimethylphenyl)-1H-pyrrole as a yellow oil.

EXAMPLE ID

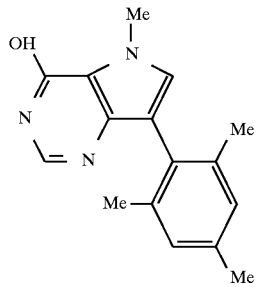

A solution of 3-Amino-2-ethoxycarbonyl-1-methyl-4-(2,4,6-trimethylphenyl)-1H-pyrrole (2.0 g, 7 mmol) in 20 mL of formamide was heated at 140° C. for 12 h. After cooling the mixture was poured into water and the resulting solid was collected and washed with more water and dried to afford 5-Methyl-7-(2,4,6-trimethylphenyl)-5H-pyrrolo[3,2-d]pyrimidin-4-ol as a tan solid melting at 230°–232° C.

EXAMPLE IE

Compound 1

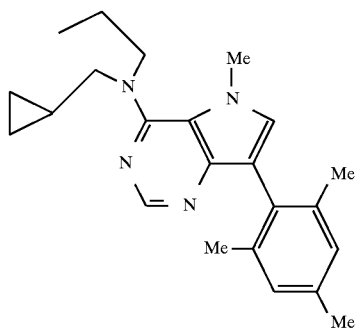

A mixture of 5-Methyl-7-(2,4,6-trimethylphenyl)-5H-pyrrolo[3,2-d]pyrimidin-4-ol (100 mg) and phosphorous oxychloride (0.5 mL) was heated at reflux for 3 hours. Excess reagent was removed in vacuo and the residual 4-chloro compound was treated with N-propylcyclopropylmethylamine (100 mg) and triethylamine (100 mg) in xylene (2 mL) and the mixture was refluxed for 8 hours.

After diluting the reaction mixture with ethyl acetate and washing with dilute bicarbonate solution, the organic layer was dried and the solvent removed in vacuo. The residue was chromatagraphed on silica gel to afford N-cyclopropylmethyl-N-propyl-5-methyl-7-(2,4,6-trimethylphenyl)-5H-pyrrolo[3,2-d]pyrimidin-4-amine (Compound 1) as an oil. The HCl salt from ethyl acetate/HCl melted at 205°–207° C.

EXAMPLE II

The following compounds are prepared essentially according to the procedures described in Examples IA–E above.

a) N,N-Dipropyl-5-methyl-7-(2,4,6-trimethylphenyl)-5H-pyrrolo[3,2-d]pyrimidin-4-amine (Compound 2) melting at 116°–118° C.
b) N,N-Diethyl-5-methyl-7-(2,4,6-trimethylphenyl)-5H-pyrrolo[3,2-d]pyrimidin-4-amine (Compound 3).
c) N,N-Dimethyl-5-methyl-7-(2,4,6-trimethylphenyl)-5H-pyrrolo[3,2-d]pyrimidin-4-amine (Compound 4).
d) N-Butyl-N-Ethyl-5-methyl-7-(2,4,6-trimethylphenyl)-5H-pyrrolo[3,2-d]pyrinidin-4-amine (Compound 5) melting at 126°–128° C.
e) N-(2-Hydroxyethyl)-N-Ethyl-5-methyl-7-(2,4,6-trimethylphenyl)-5H-pyrrolo[3,2-d]pyrimidin-4-amine (Compound 6).
f) 4-(1-Homopiperdinyl)-5-methyl-7-(2,4,6-trimethylphenyl)-5H-pyrrolo[3,2-d]pyrimidine (Compound 7) melting at 140°–142° C.
g) N-(1-Ethylpropyl)-5-methyl-7-(2,4,6-trimethylphenyl)-5H-pyrrolo[3,2d]pyrimidin-4-amine (Compound 8).
h) N-(1-Hydroxymethylpropyl)-1-methyl-7-(2,4,6-trimethylphenyl)-5H-pyrrolo[3,2d]pyrimidin-4-amine (Compound 9) melting at 118°–120° C.
i) N,N-Dipropyl-5,6-dimethyl7-(2,4,6-trimethylphenyl)-5H-pyrrolo[3,2-d]pyrimidin-4-amine (Compound 10).
j) N-(1-Hydroxymethylpropyl)-5,6-dimethyl-7-(2,4,6-trimethylphenyl)-5H-pyrrolo[3,2d]pyrimidin-4-amine (Compound 11).
k) N-(1-Hydroxymethylpropyl)-2,5-dimethyl-7-(2,4,6-trimethylphenyl)-5H-pyrrolo[3,2d]pyrimidin-4-amine (Compound 12).
l) N,N-Dipropyl-2,5-dimethyl-7-(2,4,6-trimethylphenyl)-5H-pyrrolo[3,2-d]pyrimidin-4-amine (Compound 13).
m) N-Cyclopropylmethyl-N-propyl-6-chloro-5-methyl-7-(2,4,6-trimethylphenyl)-5H-pyrrolo[3,2-d]pyrimidin-4-amine (Compound 14).
n) N-Cyclopropylmethyl-N-propyl-2-choro-5-methyl-7-(2,4,6-trimethylphenyl)-5H-pyrrolo[3,2-d]pyrimidin-4-amine (Compound 15).
o) N-Cyclopropylmethyl-N-propyl-6-bromo-5-methyl-7-(2,4,6-trimethvlphenyl)-5H-pyrrolo[3,2-d]pyrimidin-4-amine (Compound 16).
p) N-Cyclopropylmethyl-N-propyl-6-thiomethyl-5-methyl-7-(2,4,6-trimethylphenyl)-5H-pyrrolo[3,2-d]pyrimidin-4-amine (Compound 17).
q) N-Cyclopropylmethyl-N-propyl-2-thiomethyl-5-methyl-7-(2,4,6-trimethylphenyl)-5H-pyrrolo[3,2-d]pyrimidin-4-amine (Compound 18).
r) N-Cyclopropyl methyl-N-propyl-2-chloro-5-methyl-7-(2,4,6-trimethylphenyl)-5H-pyrrolo[3,2-bpyridin-4-amine (Compound 19).
s) N-Cyclopropylmethyl-N-propyl-5-methyl-7-(2,4,6-trimethylphenyl)-5H-pyrrolo[3,2-bpyridin-4-amine (Compound 20).
t) N-(1-Hdroxymethylpropyl)-5-methyl-7-(2,4,6-trimethylphenyl)-5H-pyrrolo[3,2bpyridin-4-amine (Compound 21).
u) N-Cyclopropylmethyl-N-propyl-5-amino-9-(2,4,6-trimethylphenyl)-1,2-dihydro-3H-pyrimido[5,4-e]pyrrolizine (Compound 22).
v) N-(1-Hydroxymethylpropyl)-5-amino-9-(2,4,6-trimethylphenyl)-1,2-dihydro-3H-pyrimido[5,4-e]pyrrolizine (Compound 23).
w) N-Cyclopropylmethyl-N-propyl-5-amino-7-methyl-9-(2,4,6-trimethylphenyl)-1,2-dihydro-3H-pyrimido[5,4-e]pyrrolizine (Compound 24).
x) N-Cyclopropylmethyl-N-propyl-5-amino-9-(2,4-dichlorophenyl)-1,2-dihydro-3H-pyrimido[5,4-e]pyrrolizine (Compound 25).
y) N,N-Dipropyl-5-methyl-7-(2,4-dichlorophenyl)-5H-pyrrolo[3,2-d]pyrimidin-4-amine (Compound 26).
z) N-Cyclopropylmethyl-N-propyl-5-amino-9-(2,4,6-trimethylphenyl)-1,2-dihydro-3H-pyrido[2,3-e]pyrrolizine (Compound 27).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

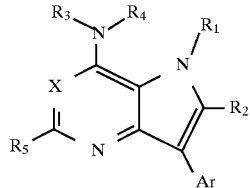

or the pharmaceutically acceptable salts thereof wherein
Ar is phenyl, 2-, 3-, or 4-pyridyl, 2- or 3-thienyl, 4- or 5-pyrimidyl, each of which is mono-, di-, or trisubstituted with halogen, hydroxy, lower alky, or lower alkoxy, with the proviso that at least one of the ortho positions of the Ar substituent is substituted;

X is CH or nitrogen;

$R_1$ is lower alkyl;

$R_2$ is hydrogen, halogen, lower alkyl, lower alkoxy, or thioalkoxy; or $R_1$ and $R_2$ taken together represent —(CH$_2$)$_n$—A—(CH$_2$)$_m$—,
where n is 2, 3 or 4, A is methylene, oxygen, sulfur or NR$_6$, where R$_6$ is lower alkyl, and
m is 0, 1 or 2;

$R_3$ and $R_4$ are the same or different and represent hydrogen or lower alkyl;

phenyl, 2-, 3-, or 4-pyridyl, 2-, or 3-thienyl, or 2-, 4-, or 5-pyrimidyl, each of which is mono- or disubstituted with halogen, hydroxy, lower alkyl, or lower alkoxy;
phenyl lower alkyl, 2-, 3-, or 4-pyridyl lower alkyl, 2- or 3-thienyl lower alkyl, or 2-, 4-, or 5-pyrimidyl lower alkyl;
cycloalkyl having 3–8 carbon atoms or cycloalkyl lower alkyl where the cycloalkyl portion has 3–8 carbon atoms;
2-hydroxyethyl or 3-hydroxypropyl optionally mono or disubstituted with lower alkyl with the proviso that not both $R_3$ and $R_4$ are hydrogen; or
$R_3$ and $R_4$ taken together represent —$(CH_2)_n$—A—$(CH_2)_m$—
where n is 2, or 3,
A is methylene, 1,2 phenylene, oxygen, sulfur or $NR_6$, wherein $R_6$ is lower alkyl, phenyl, 2-, 3-, or 4-pyridyl, 2- or 3-thienyl or 2-, 4-, or 5-pyrimidyl, phenyl lower alkyl, 2-, 3-, or 4-pyridyl lower alkyl, 2- or 3-thienyl lower alkyl, or 2-, 4-, or 5-pyrimidyl lower alkyl, and
m is 1, 2 or 3;
$R_5$ is hydrogen, halogen, lower alkyl, lower alkoxy, or thioalkoxy.

2. A compound of the formula:

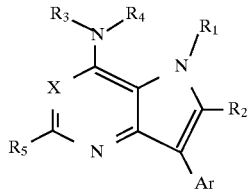

or the pharmaceutically acceptable salts thereof wherein
Ar is phenyl, 2-, 3-, or 4-pyridyl, 2- or 3-thienyl, 4- or 5-pyrimidyl, each of which is mono-, di-, or trisubstituted with halogen, hydroxy, lower alkyl, or lower alkoxy, with the proviso that at least one of the ortho positions of the Ar substituent is substituted;
X is CH or nitrogen;
$R_1$ is lower alkyl;
$R_2$ is hydrogen, halogen, lower alkyl, lower alkoxy, or thioalkoxy; or
$R_3$ and $R_4$ are the same or different and represent hydrogen or lower alkyl;
phenyl, 2-, 3-, or 4-pyridyl, 2-, or 3-thienyl, or 2-, 4-, or 5-pyrimidyl, each of which is mono- or disubstituted with halogen, hydroxy, lower alkyl, or lower alkoxy; phenyl lower alkyl, 2-, 3-, or 4-pyridyl lower alkyl, 2- or 3-thienyl lower alkyl, or 2-, 4-, or 5-pyrimidyl lower alkyl;
cycloalkyl having 3–8 carbon atoms or cycloalkyl lower alkyl where the cycloalkyl portion has 3–8 carbon atoms;
2-hydroxyethyl or 3-hydroxypropyl optionally mono or disubstituted with lower alkyl with the proviso that not both $R_3$ and $R_4$ are hydrogen;
$R_3$ and $R_4$ taken together represent —$(CH_2)_n$—A—$(CH_2)_m$—
where n is 2, or 3,
A is methylene, 1,2 phenylene, oxygen, sulfur or $NR_6$, wherein $R_6$ is lower alkyl; and
m is 1, 2 or 3; and $R_5$ is hydrogen, halogen, lower alkyl, lower alkoxy, or thioalkoxy.

3. A compound of the formula:

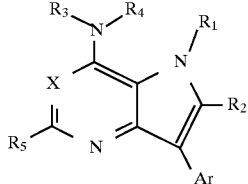

or the pharmaceutically acceptable salts thereof wherein
Ar is phenyl mono-, di-, or trisubstituted with halogen, hydroxy, lower alkyl or lower alkoxy, with the proviso that at least one of the ortho positions of the Ar substituent is substituted;
X is nitrogen;
$R_1$ is lower alkyl;
$R_2$ is hydrogen, halogen, lower alkyl, lower alkoxy, or thioalkoxy; or
$R_3$ and $R_4$ are the same or different and represent hydrogen or lower alkyl;
cycloalkyl having 3–8 carbon atoms or cycloalkyl lower alkyl where the cycloalkyl portion has 3–8 carbon atoms;
2-hydroxyethyl or 3-hydroxypropyl optionally mono or disubstituted with lower alkyl with the proviso that not both $R_3$ and $R_4$ are hydrogen; or
$R_3$ and $R_4$ taken together represent —$(CH_2)_n$—A—$(CH_2)_m$—
where n is 2, or 3,
A is methylene, 1,2 phenylene, oxygen, sulfur or $NR_6$, wherein $R_6$ is lower alkyl; and
m is 1, 2 or 3;
$R_5$ is hydrogen, halogen, lower alkyl, lower alkoxy, or thioalkoxy.

4. A compound of the formula:

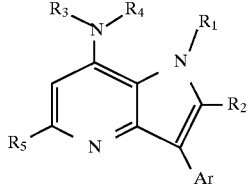

wherein
Ar is phenyl mono-, di-, or trisubstituted with halogen, hydroxy, lower alkyl, or lower alkoxy, with the proviso that at least one of the ortho positions of the Ar substituent is substituted;
$R_1$ is lower alkyl;
$R_2$ is hydrogen, halogen, lower alkyl, lower alkoxy, or thioalkoxy; or
$R_3$ and $R_4$ are the same or different and represent hydrogen or lower alkyl;
cycloalkyl having 3–8 carbon atoms or cycloalkyl lower alkyl where the cycloalkyl portion has 3–8 carbon atoms;
2-hydroxyethyl or 3-hydroxypropyl optionally mono or disubstituted with lower alkyl with the proviso that not both $R_3$ and $R_4$ are hydrogen; or
$R_3$ and $R_4$ taken together represent —$(CH_2)_n$—A—$(CH_2)_m$— where n is 2, or 3,

A is methylene, 1,2 phenylene, oxygen, sulfur or $NR_6$, wherein $R_6$ is lower alkyl; and m is 1,2 or 3;

$R_5$ is hydrogen, halogen, lower alkyl, lower alkoxy, or thioalkoxy.

5. A compound according to claim 1 wherein X is N.

6. A compound according to claim 1 wherein X is CH.

7. A compound according to claim 5 wherein $R_1$ and $R_2$ taken together represent —$(CH_2)_n$—A—$(CH_2)_m$— where n is 2, 3 or 4, A is methylene, oxygen, sulfur or NMe, and m is 0, 1 or 2.

8. A compound according to claim 6 wherein $R_1$ and $R_2$ taken together represent —$(CH_2)_n$—A—$(CH_2)_m$— where n is 2, 3 or 4, A is methylene, oxygen, sulfur or NMe, and m is 0, 1 or 2.

* * * * *